United States Patent [19]
Fischell et al.

[11] Patent Number: 5,759,174
[45] Date of Patent: Jun. 2, 1998

[54] ANGIOPLASTY BALLOON WITH AN EXPANDABLE EXTERNAL RADIOPAQUE MARKER BAND

[75] Inventors: Robert E. Fischell, Dayton, Md.; David R. Fischell, Fair Haven, N.J.; Tim A. Fischell, Richland, Mich.

[73] Assignee: Cathco, Inc., Dayton, Md.

[21] Appl. No.: 790,447

[22] Filed: Jan. 29, 1997

[51] Int. Cl.⁶ .................................................. A61M 29/00
[52] U.S. Cl. .......................... 604/96; 604/104; 604/280; 606/199; 606/198; 623/1; 128/656
[58] Field of Search ........................ 604/96, 100, 101, 604/104–106, 264, 280; 606/191, 192, 194, 198, 195; 623/1; 128/656–658

[56] References Cited

U.S. PATENT DOCUMENTS

| | | | |
|---|---|---|---|
| 4,733,665 | 3/1988 | Palmaz | 606/108 |
| 4,739,762 | 4/1988 | Palmaz | 604/96 X |
| 4,793,359 | 12/1988 | Sharrow | 128/658 |
| 4,798,586 | 1/1989 | Stevens | 604/96 |
| 4,969,458 | 11/1990 | Wiktor | 606/194 |
| 4,976,690 | 12/1990 | Solar et al. | 604/96 |
| 5,015,230 | 5/1991 | Martin et al. | 604/96 |
| 5,037,427 | 8/1991 | Harada et al. | 606/108 |
| 5,092,877 | 3/1992 | Pinchuk | 623/1 |
| 5,102,417 | 4/1992 | Palmaz | 606/195 |
| 5,197,978 | 3/1993 | Hess | 623/1 |
| 5,201,754 | 4/1993 | Crittenden et al. | 606/194 |
| 5,222,969 | 6/1993 | Gillis | 606/194 |
| 5,342,307 | 8/1994 | Euteneuer et al. | 604/103 |
| 5,342,348 | 8/1994 | Kaplan | 604/891.1 |
| 5,421,955 | 6/1995 | Lau et al. | 216/48 |
| 5,439,446 | 8/1995 | Barry | 604/96 |
| 5,449,373 | 9/1995 | Pinchasik et al. | 606/198 |
| 5,484,449 | 1/1996 | Amundson | 606/108 |
| 5,554,181 | 9/1996 | Das | 623/1 |
| 5,571,086 | 11/1996 | Kaplan et al. | 604/96 |
| 5,591,197 | 1/1997 | Orth et al. | 606/198 |
| 5,603,721 | 2/1997 | Lau et al. | 606/195 |
| 5,607,442 | 3/1997 | Fischell et al. | 606/191 |
| 5,609,627 | 3/1997 | Goicoechea et al. | 623/1 |

Primary Examiner—Michael Powell Buiz
Assistant Examiner—Chalin Smith

[57] ABSTRACT

An expandable external radiopaque marker band is situated external to the balloon of a balloon angioplasty catheter typically at the balloon's longitudinal center. When the balloon is inflated to dilate an arterial stenosis, the external radiopaque marker band is moved radially outward by the balloon thereby forcing the external radiopaque marker band into the arterial wall. When the balloon is then deflated, the external radiopaque marker band remains in place against the wall of the dilated stenosis. The balloon angioplasty catheter can then be removed from the artery while the expanded external radiopaque marker band remains in place to indicate (typically) the center position of the dilated stenosis. The external radiopaque marker band is typically made from a dense, radiopaque metal such as tantalum, gold, platinum or an alloy of those dense metals.

17 Claims, 5 Drawing Sheets

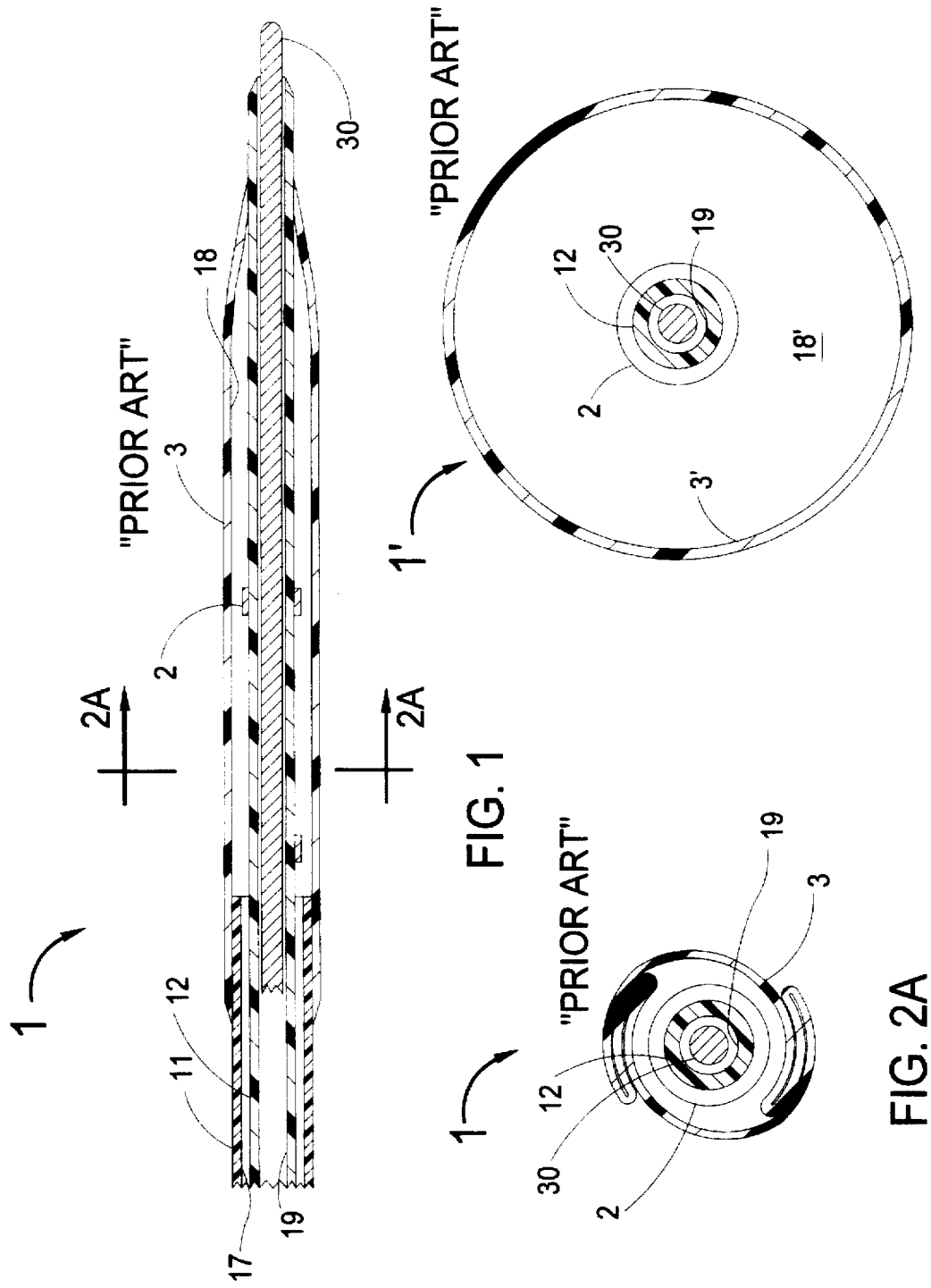

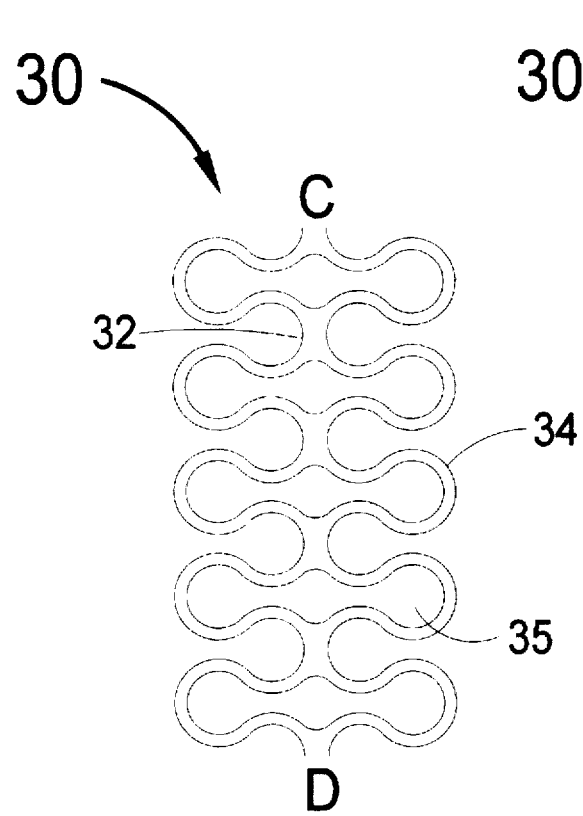
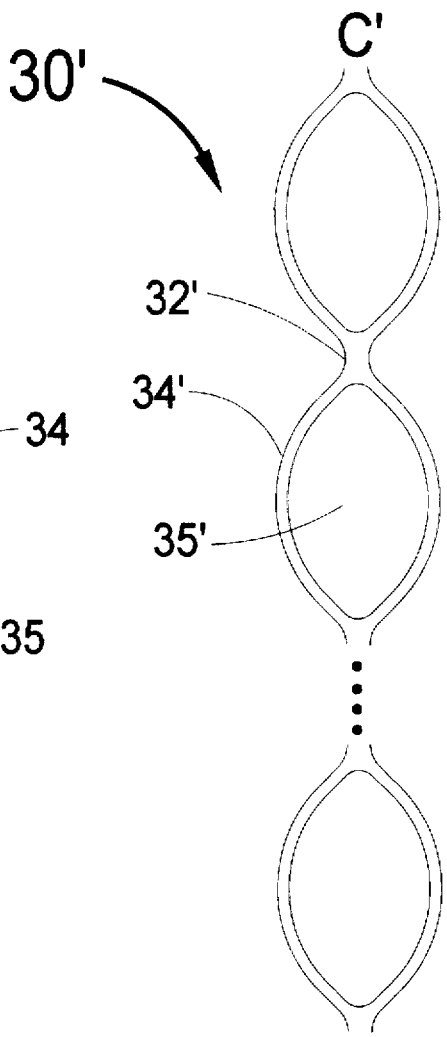
FIG.11
FIG. 12

ANGIOPLASTY BALLOON WITH AN EXPANDABLE EXTERNAL RADIOPAQUE MARKER BAND

FIELD OF USE

This invention is in the field of balloon catheter devices to dilate an arterial stenosis.

BACKGROUND OF THE INVENTION

Prior art balloon angioplasty catheters have utilized a radiopaque marker band located within and at the longitudinal center of an angioplasty balloon to assist an interventional cardiologist in placing the balloon at the location of an arterial stenosis prior to balloon inflation. When the balloon is inflated, it dilates the stenosis and then the balloon angioplasty catheter is removed from the artery. When the balloon angioplasty catheter is removed, nothing is left inside the dilated stenosis to indicate the longitudinal center of that dilated stenosis.

SUMMARY OF THE INVENTION

The present invention is an expandable external radiopaque marker band that is situated external to the balloon of a balloon angioplasty catheter typically at the balloon's longitudinal center. When the balloon is inflated to dilate an arterial stenosis, the external radiopaque marker band is moved radially outward by the balloon thereby forcing the external radiopaque marker band into the arterial wall. When the balloon is then deflated, the external radiopaque marker band remains in place, imbedded into the wall of the dilated stenosis. The balloon angioplasty catheter can then be removed from the artery while the expanded external radiopaque marker band remains in place to indicate (typically) the center position of the dilated stenosis.

Thus, an object of this invention is to have an external radiopaque marker band that remains in place to indicate the position of a dilated stenosis after the balloon angioplasty catheter that was used to dilate that stenosis has been removed from the patient's body.

These and other important objects and advantages of this invention will become apparent from the detailed description of the invention and the associated drawings provided herein.

BRIEF DESCRIPTION OF THE DRAWINGS

FIG. 1 is a longitudinal cross section of a "Prior Art" balloon angioplasty catheter having an internal radiopaque marker band located inside the angioplasty balloon of the balloon angioplasty catheter.

FIG. 2A is an enlarged transverse cross section of the "Prior Art" balloon angioplasty catheter of FIG. 1 at section 2—2.

FIG. 2B is an enlarged transverse cross section of the "Prior Art" balloon angioplasty catheter shown with the balloon in its inflated state.

FIG. 11 is a flat, layout view of another embodiment of an external radiopaque marker band shown in its unexpanded state.

FIG. 12 is a flat, layout view of the external radiopaque marker band of FIG. 11 shown in its expanded state.

DETAILED DESCRIPTION OF THE INVENTION

Figure 3:
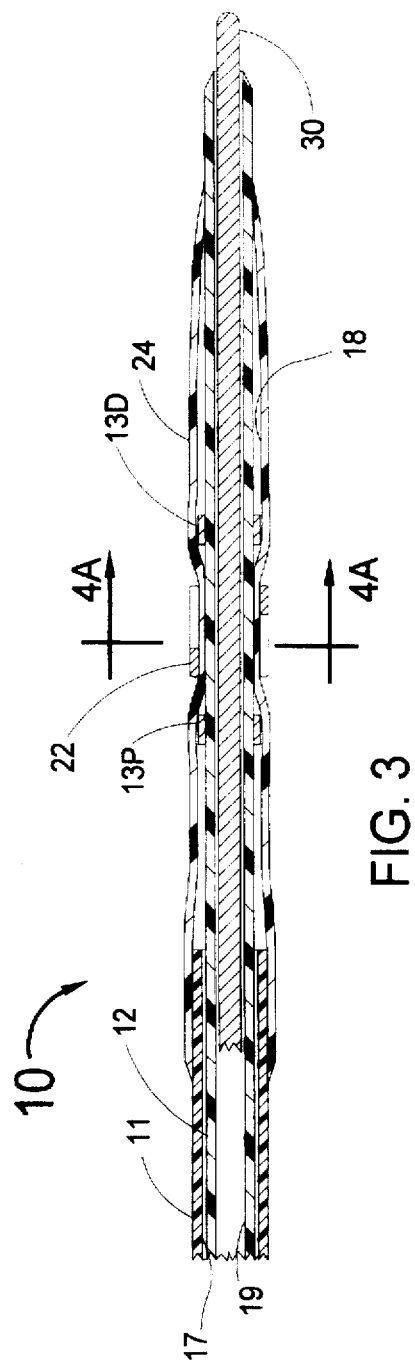
FIG. 3 is a longitudinal cross section of a distal section of a balloon angioplasty catheter with an external radiopaque marker band located at the longitudinal center of the angioplasty balloon.

FIGS. 1, 2A and 2B illustrate a typical "Prior Art" balloon angioplasty catheter 1 having an internal radiopaque marker band 2, an angioplasty balloon 3, an outer shaft 11, an inner shaft 12 and a guide wire lumen 19 through which a guide wire 30 can be slideably moved. The annular passageway 17 is used for inflation fluid to inflate at high pressure the balloon 3 by placing the inflation fluid through the passageway 17 into the balloon chamber 18. Balloon deflation is accomplished by removing the fluid through the passageway 17. FIG. 2B shows the inflated balloon 3' and the filled balloon chamber 18' of the inflated state balloon angioplasty catheter 1'.

Figure 4B:
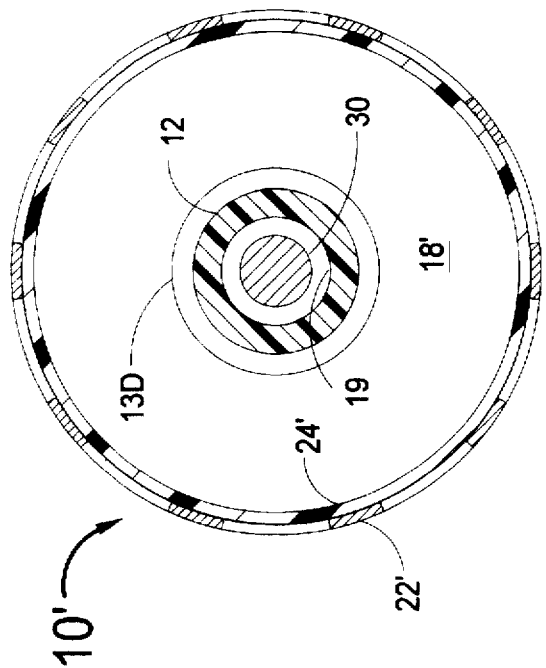
FIG. 4B is an enlarged transverse cross section of the balloon angioplasty catheter of FIGS. 3 and 4A shown with the balloon in its expanded state.
Figure 4A:
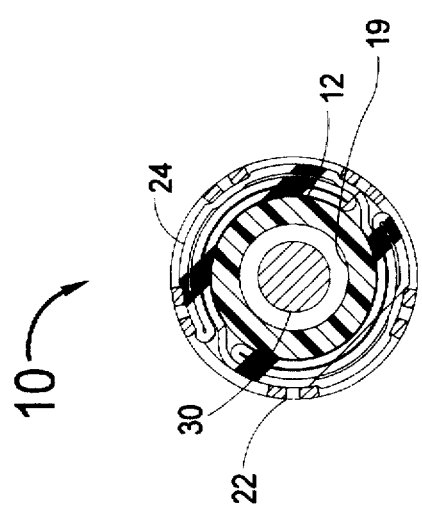
FIG. 4A is an enlarged transverse cross section of the balloon angioplasty catheter of FIG. 3 at section 4—4.

FIGS. 3, 4A and 4B illustrate the present invention in the form of a balloon angioplasty catheter 10 having an internal proximal radiopaque marker band 13P, an internal distal radiopaque marker band 13D, an external radiopaque marker band 22, an inflatable balloon 24 whose proximal end is joined to the distal end of the outer shaft 11 and whose distal end is joined to the distal end of the inner shaft 12. As with prior art balloon angioplasty catheter 1, the present invention utilizes an annular passageway 17 to inflate and deflate the balloon chamber 18. FIGS. 3 and 4A show the distal section of the balloon angioplasty catheter 10 in uninflated state. FIG. 4B is a transverse cross section of the balloon angioplasty catheter 10' showing the inflated balloon 24', inflated balloon chamber 18' and the expanded external radiopaque marker band 22'. The internal radiopaque marker bands 13P and 13D indicate the position of the balloon 24 or 24' after the external radiopaque marker band has been paced into the wall of a dilated arterial stenosis.

Figure 5:
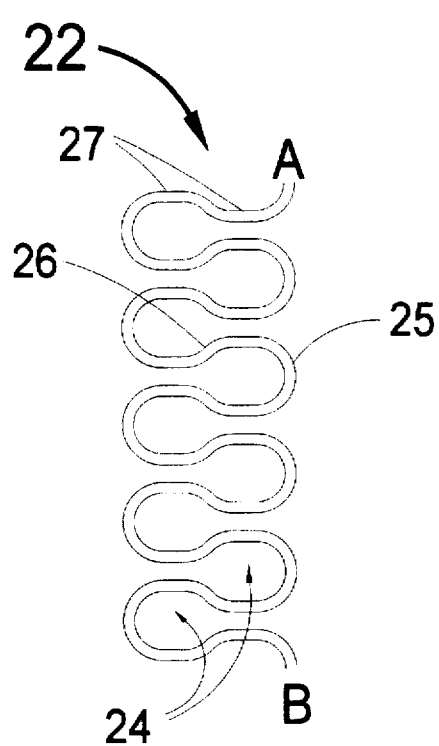
FIG. 5 is a flat, layout view of the external radiopaque marker band in its unexpanded state.
Figure 7:
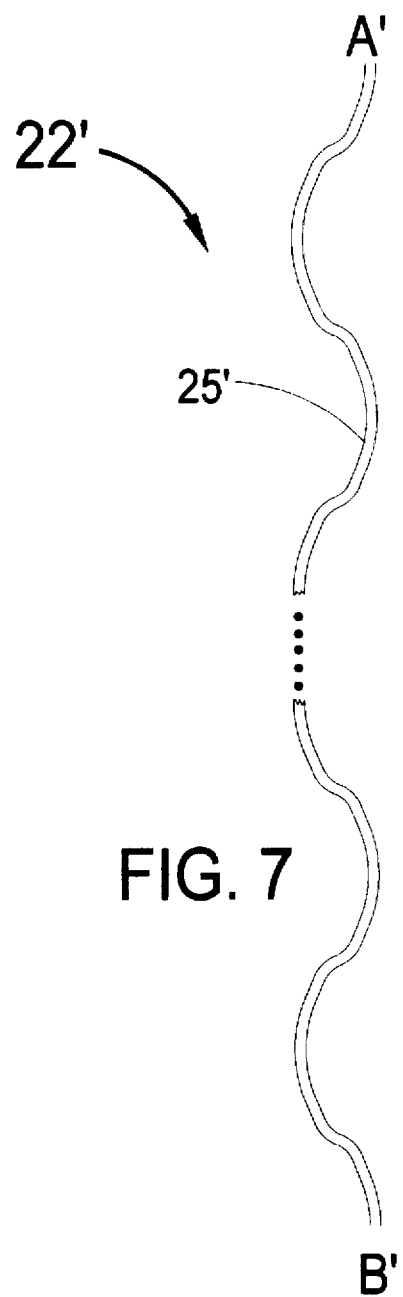
FIG. 7 is a flat, layout view of the external radiopaque marker band in its expanded state.

FIG. 5 is a layout view of one form of external radiopaque marker band 22. FIG. 5 shows the external radiopaque marker band 22 with ten half-segments 24, each half-segment 24 consisting of one half-circle 25 and two curved sections 26 each of which is joined by straight sections 27 to the ends of each half-circle 25. Although FIG. 5 shows the external radiopaque marker band 22 as it would look if it were laid out flat, it should be understood that in fact the unexpanded external radiopaque marker band forms a short, cylindrically shaped structure that when fully expanded, becomes a single wire, ring-like structure which is the expanded external radiopaque marker band 22' as shown in FIG. 7. It should also be understood that the ends "A" and "A'" of FIGS. 5 and 7 are in fact connected respectively to the ends "B" and "B'" to form a closed structure. The diameter of the unexpanded external radiopaque marker band structure is typically between 0.5 and 1.5 mm and the width of such a cylinder would typically lie between 0.3 and 4 mm depending somewhat on the diameter of the artery into which the external radiopaque marker band 22 is to be placed. The width of the external radiopaque marker band 22 also depends on the specific design that is selected.

Figure 6:
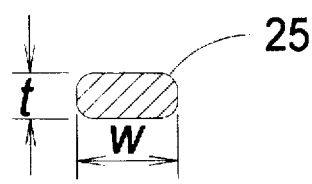
FIG. 6 is a highly enlarged transverse cross section of the external radiopaque marker band of FIG. 5 at section 6—6.

FIG. 6 shows a cross section of the external radiopaque marker band 22 at section 6—6 of FIG. 5. The dimension "t" would typically be between 0.02 to 0.2 mm; and the typical width "w" would be between 0.04 and 0.5 mm.

Figure 8:
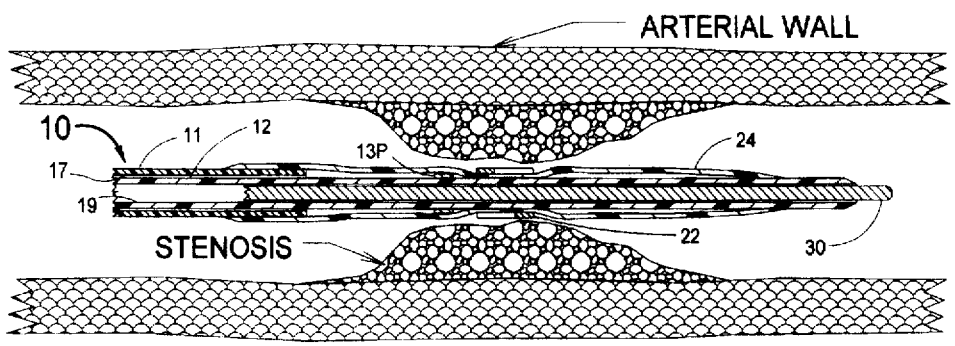
FIG. 8 is a longitudinal cross section of a distal section of the balloon angioplasty catheter with external radiopaque marker band shown within an arterial stenosis prior to balloon inflation.
Figure 9:
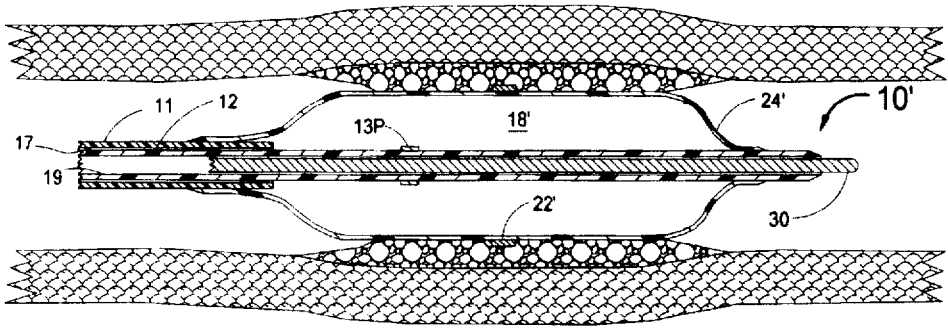
FIG. 9 is a longitudinal cross section of a distal section of the balloon angioplasty catheter with external radiopaque marker band shown with the balloon inflated thus dilanting the arterial stenosis and expanding the external radiopaque marker band.

FIG. 8 shows the uninflated balloon angioplasty catheter 10 of the present invention placed within an arterial stenosis. When the balloon 24 is expanded using a contrast medium solution to a pressure between 5 and 20 atmospheres, one obtains an expanded balloon 24' and expanded external radiopaque marker band 22' as seen in FIG. 9. This is conventional balloon angioplasty used to dilate an arterial stenosis. It should be noted that there is only one internal radiopaque marker band 13P in FIG. 8. This is sometimes done to decrease the profile of the distal half of the balloon 24 for easier passage through a tight stenosis.

Figure 10:
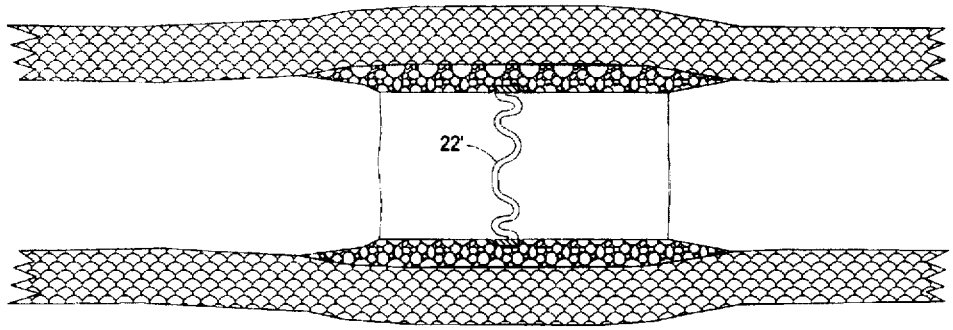
FIG. 10 is a longitudinal cross section of the dilated arterial stenosis shown with the balloon angioplasty catheter removed and the external radiopaque marker in its expanded state situated at the longitudinal center of the dilated stenosis.

FIG. 10 shows the deployed external radiopaque marker band 22' as it would look after the balloon angioplasty catheter 10 is removed from the patient's body. It should be noted that to be an effective marker band as opposed to being a stent, the longitudinal length of the marker band 22' must be less than one-third the length of the cylindrical portion of the inflated angioplasty balloon 24' as shown in FIG. 9. After stenotic dilation, the balloon 24' is deflated and the balloon angioplasty catheter 10 is removed from the patient's body. Unlike prior art radiopaque marker bands that lie within an angioplasty balloon which become removed when the balloon angioplasty catheter is removed, the external radiopaque marker band 22' of the present invention remains within the dilated stenosis typically at or near the longitudinal center of the stenosis. This makes it possible to perform additional dilatation of the stenosis and/or placement of an intravascular stent without requiring the operator to use additional injections of contrast medium to relocate the stenosis that is to have one or more additional treatments. Among the additional treatments are additional balloon dilatation and/or the placement of an intravascular stent. Furthermore, this marker could be used in conjunction with catheter based irradiation or drug delivery to assist in the placement of the radioactive source or a drug delivery balloon. The use of this invention saves the cost of additional contrast medium, decreases the amount of contrast medium released into the patient's vascular system and shortens the time for the interventional procedure. Additionally, because it is often difficult to discern exactly where a dilated stenosis was located, the expanded external radiopaque marker band 22' can can be used to clearly indicate any desired location(s) to assist in performing any subsequent procedure.

The external radiopaque marker band would typically be made from a high density metal having a specific gravity greater than 9.0 such as tantalum, gold or platinum or an alloy that includes such a high density metal. Furthermore, this technique can be used with either "over-the-wire" or "rapid exchange" types of balloon angioplasty catheters both of which are well known in the art of balloon angioplasty.

FIG. 11 is a flat, layout view of an alternative embodiment, unexpanded, external radiopaque marker band 30 having straight struts 32 and curved struts 34 that form a multiplicity of closed perimeter cells 35. When expanded by an inflatable balloon, the expanded external radiopaque marker band 30' has straight struts 32', curved struts 34' which together formed the elongated cells 35'. It should be understood that the external radiopaque marker bands 30 and 30' are really in the form of a cylinders with points "C" and "C'" connected respectively to points "D" and "D'".

Although the external radiopaque marker band has been shown here to mark the longitudinal center of a dilated stenosis, it is also envisioned that one or more external radiopaque marker bands could be used to mark any specific location in any artery, vein or any other vessel of the human body such as billiary duct, urethra, ureter, fallopian tube, etc. Furthermore, catheters of any type could be used for deployment of an external radiopaque marker band, for example a balloon catheter that used an elastic balloon, or a catheter having a distal mechanical device for deployment of a radiopaque marker band could also be used.

The external radiopaque marker band is distinctly different from a stent in that a stent has a length in the longitudinal direction of at least 7 mm where the external radiopaque marker band must be no more than 4 mm in length in order not to interfere with the ability of a pre-dilation balloon on a balloon angioplasty catheter to dilate a tight stenosis. Furthermore, the optimum external radiopaque marker band is not more than one cell wide in the longitudinal direction and still more optimally at least some of its circumferential length would be only one wire wide.

As with many implantable devices placed into the wall of a blood vessel, the external radiopaque marker band could have either an antithrombogenic coating and/or a slippery coating. Also, it is conceived that such a marker could be non-coaxilly attached, for example within a fold of an angioplasty balloon, and then released into the arterial wall when the balloon is inflated.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A balloon catheter having a distal section with an inflatable balloon located at that distal section and having one expandable external radiopaque marker band located coaxially around and external to the inflatable balloon, the longitudinal length of the external radiopaque marker band when it is deployed being less than one-third the length of the cylindrical section of the balloon when the balloon is inflated.

2. The balloon catheter of claim 1 wherein the one external radiopaque marker band is located at the longitudinal center of the balloon.

3. The balloon catheter of claim 1 wherein the balloon catheter is a balloon angioplasty catheter and the balloon is an angioplasty balloon.

4. The balloon catheter of claim 1 wherein the balloon catheter is an elastic balloon catheter and the balloon is an elastic balloon.

5. The balloon catheter of claim 1 wherein the balloon catheter also has at least one non-expandable radiopaque marker band located within the balloon of the balloon catheter.

6. The balloon catheter of claim 5 wherein there are two non-expandable radiopaque marker bands located inside the balloon of the balloon catheter.

7. The balloon catheter of claim 5 wherein there is only one non-expandable radiopaque marker band and it is located proximal to the longitudinal position of the expandable external radiopaque marker band.

8. The balloon catheter of claim 1 wherein the external radiopaque marker band is fabricated from a metal having a specific gravity greater than 9.0.

9. The balloon catheter of claim 8 wherein the metal is pure tantalum.

10. The balloon catheter of claim 8 wherein the metal is an alloy containing tantalum.

11. The balloon catheter of claim 8 wherein the metal is pure gold.

12. The balloon catheter of claim 8 wherein the metal is an alloy of gold.

13. The balloon catheter of claim 8 wherein the metal is pure platinum.

14. The balloon catheter of claim 8 wherein the metal is an alloy of platinum.

15. A method for marking a specific location in a blood vessel of a human subject, the method comprising:

(a) placing a balloon angioplasty catheter having a distal section and having at that distal section an angioplasty balloon with one external radiopaque marker band mounted externally to and coaxially around the angioplasty balloon through the blood vessel until the external radiopaque marker band is situated at a position within the blood vessel that is to be marked;

(b) inflating the angioplasty balloon thus radially expanding the external radiopaque marker band at the site to be marked the external radiopaque marker band then having a longitudinal length that is less than one-third the length of the cylindrical section of the inflated balloon;

(c) deflating the angioplasty balloon and removing the balloon angioplasty catheter from the patient's blood vessel; and (d) retaining the radially deployed external radiopaque marker band at the location within the blood vessel that was to be marked.

16. The method of claim 15 wherein the site to be marked is at the center of an arterial stenosis.

17. The method of claim 15 wherein the specific location within the blood vessel that is to be marked is at an arterial stenosis and the inflation of the angioplasty balloon simultaneously dilates the stenosis and deploys the external radiopaque marker band radially outward into the wall of the dilated stenosis thus providing a radiopaque marker at one specific location.

* * * * *